United States Patent

Kraatz

Patent Number: 4,950,767
Date of Patent: Aug. 21, 1990

[54] PROCESS FOR THE PREPARATION OF THE (−)-ANTIPODE OF (E)-1-CYCLOHEXYL-4,4-DIMETHYL-3-HYDROXY-2-(1,2,4-TRIAZOL-1-YL)-PENT-1-ENE

[75] Inventor: Udo Kraatz, Leverkusen, Fed. Rep. of Germany

[73] Assignee: Bayer Aktiengesellschaft, Leverkusen, Fed. Rep. of Germany

[21] Appl. No.: 265,191

[22] Filed: Oct. 31, 1988

Related U.S. Application Data

[62] Division of Ser. No. 25,297, Mar. 12, 1987, Pat. No. 4,808,725.

[30] Foreign Application Priority Data

Mar. 19, 1986 [DE] Fed. Rep. of Germany ....... 3609152

[51] Int. Cl.$^5$ ............................................ C07D 207/12
[52] U.S. Cl. .................................................... 548/570
[58] Field of Search ......................................... 548/570

[56] References Cited

U.S. PATENT DOCUMENTS

| | | | |
|---|---|---|---|
| 1,158,496 | 11/1915 | Hess | 548/570 X |
| 3,006,925 | 10/1961 | Feldkamp et al. | 548/570 |
| 3,479,370 | 11/1969 | Lunsford et al. | 548/570 X |
| 3,651,085 | 3/1972 | Lunsford et al. | 548/570 X |
| 4,248,884 | 2/1981 | Legrand et al. | 548/570 X |
| 4,592,772 | 6/1986 | Kraatz et al. | 548/570 X |
| 4,625,038 | 11/1986 | Thottathil | 548/570 |
| 4,661,512 | 4/1987 | Laruelle et al. | 548/533 X |
| 4,808,725 | 2/1989 | Kraatz | 548/262 |

FOREIGN PATENT DOCUMENTS

| | | | |
|---|---|---|---|
| 0054431 | 6/1982 | European Pat. Off. | |
| 0103798 | 3/1984 | European Pat. Off. | |
| 0142566 | 5/1985 | European Pat. Off. | |
| 3302122 | 7/1984 | Fed. Rep. of Germany | |
| 0021328 | 9/1969 | Japan | 548/570 |
| 0007251 | 2/1971 | Japan | 548/570 |
| 0011933 | 4/1973 | Japan | 548/570 |
| 8504401 | 10/1985 | World Int. Prop. O. | |

OTHER PUBLICATIONS

Enders et al., "Nucleophilic Alpha-Sec-Aminoalkylation . . . ", Organic Syntheses, B. 58, Dec. 1978, pp. 113–122.
90642w: Likhosherstov et al., "Aza Cycloalkanes.", Chem. Abstr. V. 67, No. 19, Nov. 1967, p. 8527.

Primary Examiner—Joseph Paul Brust
Attorney, Agent, or Firm—Sprung Horn Kramer & Woods

[57] ABSTRACT

A process for the preparation of an optically active proline derivative of the formula

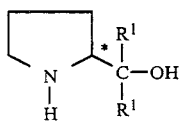

in which $R^1$ is alkyl, phenyl or benzyl, or an acid addition salt thereof, comprising reacting an S-proline ester of the formula

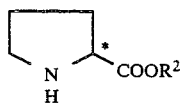

in which $R^2$ is alkyl with 1 to 4 carbon atoms, in a first stage with benzyl chloroformate of the formula

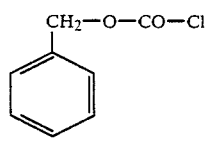

in the presence of an acid-binding agent and in the presence of a diluent, thereby to produce an ester with the S-configuration on the asymmetrically substituted carbon atom, of the formula

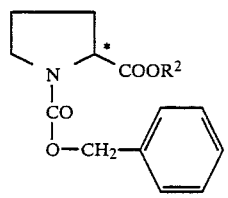

reacting such ester in a second stage with a Grignard compound of the formula

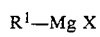

$R^1$—Mg X in which X is chlorine, bromine or iodine, in the presence of a diluent, thereby to produce an S-proline derivative of the formula

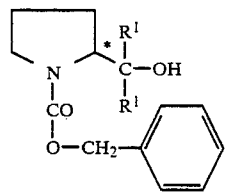

and reacting such S-proline derivative in a third stage with hydrogen in the presence of a catalyst, a diluent, and optionally an acid. The end product is new.

PROCESS FOR THE PREPARATION OF THE (−)-ANTIPODE OF (E)-1-CYCLOHEXYL-4,4-DIMETHYL-3-HYDROXY-2-(1,2,4-TRIAZOL-1-YL)-PENT-1-ENE

This is a division of application Ser. No. 025,297, filed Mar. 12, 1987, now U.S. Pat. No. 4,808,725, issued 2-28-87.

The present invention relates to a new process for the preparation of the known (−)-antipode of (E)-1-cyclohexyl-4,4-dimethyl-3-hydroxy-2-(1,2,4-triazol-1-yl)-pent-1-ene.

The (−)-antipode here is in each case to be understood as that enantiomer which rotates the plane of oscillation of linearly polarized light of the sodium D line to the left.

It has already been disclosed that the (−)-antipode of (E)-1-cyclohexyl-4,4-dimethyl-3-hydroxy-2-(1,2,4-triazol-1-yl)-pent-1-ene can be prepared by reacting the corresponding racemic compound with an optically active acid chloride, resolving the resulting ester diastereomer mixture chromatographically and hydrolyzing the ester which contains the (−)-antipode. See U.S. Pat. No. 4,592,772 issued Jun. 3, 1986. The disadvantage of this process, however, is that it is only suitable for the synthesis of small amounts of the desired antipode.

It has furthermore already been disclosed that ketones can be reduced with reducing agents in the presence of various chiral auxiliary reagents to give optically active carbinols (compare Chem. Pharm. Bull. 31 837 (1983) and EP-OS (European Published Specification) 0,054,431). It is unsatisfactory, however, that this process is not generally applicable. Thus, ketones which contain no aromatic groups can only be converted into carbinols which have an optical purity which is inadequate for practical purposes.

It is moreover known that the (−)-antipode of (E)-1-cyclohexyl-4,4-dimethyl-3-hydroxy-2-(1,2,4-triazol-1-yl)-pent-1-ene can be synthesized by reducing the (E)-isomer of 1-cyclohexyl-4,4-dimethyl-2-(1,2,4-triazol-1-yl)-pent-1-en-3-one with boron hydrides in the presence of (−)-norephedrine (compare EP-OS (European Published Specification) 142,566). A decisive disadvantage of this process, however, is that the optical purity of the desired product is relatively low.

It has now been found that the (−)-antipode of (E)-1-cyclohexyl-4,4-dimethyl-3-hydroxy-2-(1,2,4-triazol-1-yl)-pent-1-ene of the formula

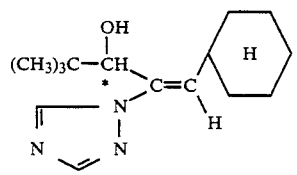

is obtained by a process in which the (E)-isomer of 1-cyclohexyl-4,4-dimethyl-2-(1,2,4-triazol-1-yl)-pent-1-en-3-one of the formula

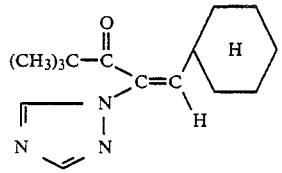

is reacted (a) with boron hydride in the presence of an optically active proline derivative of the formula

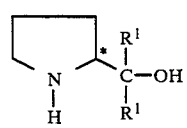

in which

R¹ represents alkyl, phenyl or benzyl, or (b) with complex borohydrides in the presence of an acid addition salt of an optically active proline derivative of the formula (III) in the presence of a diluent at temperatures between −70° C. and +60° C.

It is to be described as exceptionally surprising that the (−)-antipode of (E)-1-cyclohexyl-4,4-dimethyl-3-hydroxy-2-(1,2,4-triazol-1-yl)-pent-1-ene of the formula (I) can be prepared in a very high yield and excellent optical purity by the process according to the invention, since on the basis of the known prior art it could not be expected that the reaction leads selectively to the desired product. Above all, it was not to be expected that the reaction also proceeds virtually free from side reactions at relatively high temperatures.

The process according to the invention is distinguished by a number of advantages. Thus, the reaction components are also available in relatively large amounts and can also be handled without problems on an industrial scale. The expenditure on apparatus necessary to carry out the process is furthermore low, and working up of the reaction mixture obtained when the reaction has ended presents no difficulties. In particular, however, the (−)-antipode of (E)-1-cyclohexyl-4,4-dimethyl-3-hydroxyl-2-(1,2,4-triazol-1-yl)-pent-1-ene of the formula (I) can be prepared in a higher yield and a better optical purity by the process according to the invention than by the methods previously known.

The (−)-antipode of (E)-1-cyclohexyl-4,4-dimethyl-3-hydroxy-2-(1,2,4-triazol-1-yl)-pent-1-ene which can be prepared by the process according to the invention is unambiguously characterized by formula (I). In this formula, the asymmetrically substituted carbon atom, which represents the chirality center, is labelled by an (*). The letter "E" before the systematic name of the compound of the formula (I) expresses that the cyclohexyl radical and the 1,2,4-triazolyl radical are on opposite sides of the double bond.

If boron hydride is used as the reducing agent, S-2-(dibenzyl-hydroxymethyl)-pyrrolidine is used as the chiral auxiliary reagent and tetrahydrofuran (=THF) is used as the diluent, the course of the process according to the invention (variant a) can be represented by the following equation:

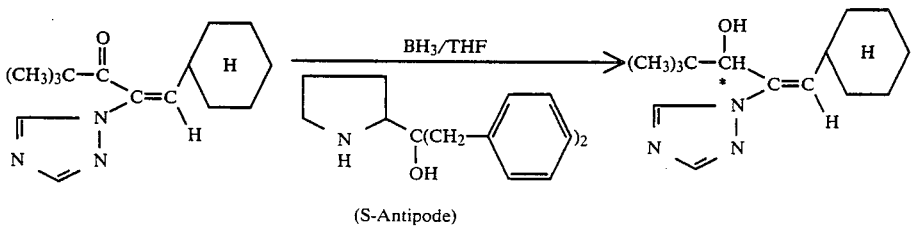

(S-Antipode)

If sodium boranate is used as the reducing agent and the hydrochloride of S-2-(dibenzyl-hydroxymethyl)-pyrrolidine is used as the chiral auxiliary reagent, the course of the process according to the invention (variant b) can in principle likewise be illustrated by the equation shown above.

The E-isomer of 1-cyclohexyl-4,4-dimethyl-2-(1,2,4-triazol-1-yl)-pent-1-en-3-one of the formula (II) required as a starting material in carrying out the process according to the invention is already known (compare DE-OS (German Published Specification) 3,222,181).

In carrying out the process according to the invention, either boron hydride (variant a) or complex borohydrides (variant b) function as the reducing agent. Sodium boranate is a preferred possible complex borohydride here.

Formula (III) provides a general definition of the optically active proline derivatives (=substituted hydroxymethyl-pyrrolidines) required as chiral auxiliary reagents in carrying out the process according to the invention (variant a). In this formula, $R^1$ preferably represents alkyl with 1 to 6 carbon atoms, phenyl or benzyl.

Possible acid addition salts of optically active proline derivatives in carrying out variant (b) of the process according to the invention are, preferably, those compounds which are formed by addition of hydrogen halide acids, such as, for example, hydrochloric or hydrobromic acid, or furthermore sulphuric acid, nitric acid, phosphoric acid or naphthalene-1,5-disulphonic acid, onto optically active compounds of the formula (III).

In the proline derivatives of the formula (III) or acid addition salts thereof which are used as chiral auxiliary reagents in carrying out the process according to the invention, the asymmetrically substituted carbon atom has the S-configuration.

The optically active proline derivatives of the formula (III) and acid addition salts thereof were not previously known. They can be prepared by a process in which either
(c) S-proline esters of the formula

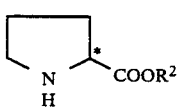  (IV)

in which
$R^2$ represents alkyl with 1 to 4 carbon atoms,
are reacted with Grignard compounds of the formula $R^1$—Mg X  (V)

in which
$R^1$ has the abovementioned meaning and
X represents chlorine, bromine or iodine, in the presence of a diluent, or
(d) S-proline esters of the formula

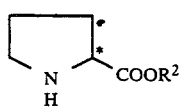  (IV)

in which
$R^2$ has the abovementioned meaning,
are reacted in a first stage with benzyl chloroformate of the formula

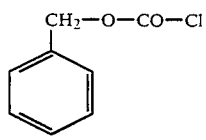  (VI)

in the presence of an acid-binding agent and in the presence of a diluent, and the resulting esters with the S-configuration on the asymmetrically substituted carbon atom, of the formula

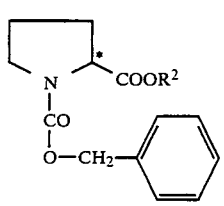  (VII)

in which
$R^2$ has the abovementioned meaning,
are then reacted in a second stage with Grignard compounds of the formula $R^1$—Mg X  (V)

in which
$R^1$ and X have the abovementioned meaning,
in the presence of a diluent, and finally the S-proline derivatives thereby obtained, of the formula

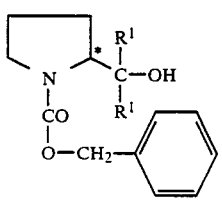  (VIII)

in which $R^1$ has the abovementioned meaning,
are reacted in a third stage with hydrogen in the presence of a catalyst and in the presence of a diluent, and, if appropriate, an acid is also added.

Formula (IV) provides a definition of the S-proline esters required as starting substances in the preparation of the optically active proline derivatives of the formula (III). In this formula, $R^2$ preferably represents methyl or ethyl. In each case those compounds which have the S-configuration on the asymmetrically substituted carbon atoms are used.

The S-proline esters of the formula (IV) are known or can be prepared in a simple manner by processes which are known in principle.

Formula (V) provides a general definition of the Grignard compounds required as reaction components in processes (c) and (d). In this formula, $R^1$ preferably has those meanings which have already been mentioned as preferred for this radical in connection with the description of the compounds of the formula (III). X represents chlorine, bromine or iodine.

The Grignard compounds of the formula (V) are generally known compounds of organic chemistry. Benzyl chloroformate of the formula (VI) and its use as a protective group are likewise known.

Possible diluents in carrying out process (c) are all the customary inert organic solvents. Solvents which can preferably be used are ethers, such as diethyl ether, tetrahydrofuran and dioxane.

The reaction temperatures can be varied within a certain range in carrying out process (c). The reaction is in general carried out at temperatures between $-10°$ C. and $+80°$ C., preferably between $0°$ C. and $+60°$ C.

In carrying out process (c), 5 to 10 mols of Grignard compound of the formula (V) are employed per mol of S-proline ester of the formula (IV). Working up is carried out by customary methods. In general, a procedure is followed in which the reaction mixture is hydrolyzed with water, aqueous ammonium chloride solution is then added and the organic phase is separated off, washed, dried and, after being concentrated, distilled.

Possible acid-binding agents in carrying out the first stage of process (d) are all the customary acid acceptors. Acid acceptors which can preferably be used are tertiary amines, such as trietyylamine, N,N-dimethylaniline, pyridine, N,N-dimethylaminopyridine, diazabicyclooctane (DABCO), diazabicyclononene (DBN) or diazabicycloundecene (DBU).

Possible diluents in carrying out the first stage of process (d) are all the customary inert organic solvents. Solvents which can preferably be used are ethers, such as diethyl ether, tetrahydrofuran or dioxane.

The reaction temperatures can be varied within a certain range in carrying out the first stage of process (d). The reaction is in general carried out at temperatures between $-10°$ C. and $+60°$ C., preferably between $0°$ C. and $+50°$ C.

In carrying out the first stage of process (d), in general 1 to 1.5 mols of benzyl chloroformate of the formula (VI) and 1 to 1.5 mols of acid-binding agent are employed per mole of S-proline ester of the formula (IV). Working up is carried out by customary methods. In general, a procedure is followed in which water is added to the reaction mixture, the mixture is then extracted with an organic solvent of low water-solubility and the combined organic phases are washed and, after being concentrated, distilled.

Possible diluents in carrying out the second stage of process (d) are all the customary inert organic solvents. Solvents which can preferably be used are ethers, such as diethyl ether, tetrahydrofuran and dioxane.

The reaction temperatures can likewise be varied within a certain range in carrying out the second stage of process (d). The reaction is in general carried out at temperatures between $-10°$ C. and $+80°$ C., preferably between $0°$ C. and $+60°$ C.

In carrying out the second stage of process (d), in general 2 to 5 mols of Grignard compound of the formula (V) are employed per mol of a compound of the formula (VII). Working up is carried out by customary methods. In general, a procedure is followed in which the reaction mixture is hydrolyzed with water and then acidified and extracted with an organic solvent of low water-miscibility and the combined organic phases are washed and, after being dried, concentrated.

Possible catalysts in carrying out the third stage of process (d) are all the reaction accelerators customary for such reactions. Reaction accelerators which can preferably be used are palladium or platinum on charcoal.

Possible diluents in carrying out the third stage of process (d) are all the customary inert organic solvents. Solvents which can preferably be used are alcohols, such as methanol and ethanol, and furthermore ethers, such as diethyl ether, tetrahydrofuran and dioxane.

The reaction temperatures can also be varied within a certain range in carrying out the third stage of process (d). The reaction is in general carried out at temperatures between $0°$ and $40°$ C., preferably between $10°$ and $30°$ C.

In carrying out the third stage of process (d), the hydrogenation is carried out with an excess of hydrogen under a pressure of 1 to 10 bar. Working up is carried out by customary methods. In general, a procedure is followed in which the catalyst is filtered off, an organic solvent of low water-solubility is added to the reaction mixture which remains, if appropriate after prior acidification, and the desired product is then isolated by filtration or concentration.

Acids which are possible for the preparation of acid addition salts of the compounds of the formula (III) are, preferably, those which have already been mentioned as acids which are preferably to be added in connection with the description of these salts.

The acid addition salts of the compounds of the formula (III) can be obtained in a simple manner by customary salt formation methods, such as, for example, by dissolving a compound of the formula (III) in a suitable inert solvent and adding the acid, such as, for example, hydrochloric acid, and they can be isolated in a known manner, for example by filtration, and if appropriate purified by washing with an inert organic solvent. In the process (d) described above, acid addition salts of compounds of the formula (III) are preferably prepared by a procedure in which the acid in question and an inert organic solvent are added to the mixture obtained after hydrogenation, after removal of the catalyst, and the salt which separates out as crystals is filtered off.

Possible diluents in the process according to the invention for the preparation of the (−)-antipode of (E)-1-cyclohexyl-4,4-dimethyl-3-hydroxy-2-(1,2,4-triazol-1-yl)-pent-1-ene of the formula (I) are all the customary organic solvents for such reactions. Solvents which are preferably possible are halogenated hydrocarbons, such as methylene chloride, and furthermore ethers, such as diethyl ether, tert.-butyl methyl ether, tetrahydrofuran, dioxane and anisole.

The reaction temperatures can be varied within a certain range in carrying out the process according to the invention. The reaction is in general carried out at temperatures between −70° C. and +60° C., preferably between −30° C. and +50° C.

The process according to the invention is in general carried out under normal pressure.

In carrying out the process according to the invention, in general 1 to 4 mols, preferably 1.3 to 3 mols, of boron hydride or complex borohydride and 1 to 3 mols, preferably 1.2 to 2 mols, of optically active proline derivative of the formula (III) or an acid addition salt of an optially active proline derivative of the formula (III) are employed per mol of (E)-isomer of 1-cyclohexyl-4,4-dimethyl-2-(1,2,4-triazol-1-yl)-pent-1-en-3-one of the formula (II).

In carrying out the process according to the invention, a procedure is in general followed in which the reducing agent is added at temperatures of between −30° C. and +30° C. to a solution of the optically active proline derivative or acid addition salt of the optically active proline derivative in an organic solvent, the (E)-isomer of 1-cyclohexyl-4,4-dimethyl-2-(1,2,4-triazol-1-yl)-pent-1-en-3-one of the formula (II) is then added at temperatures between 20° and 50° C. and the mixture is stirred at temperatures between 20° and 50° C. for several hours. Working up is carried out by customary methods. In general, a procedure is followed in which water or an acid and water are added to the reaction mixture, the mixture is then extracted with an organic solvent of low water-solubility and the combined organic phases are concentrated, if appropriate after prior washing. The residue which remains can be further purified by digestion with suitable organic solvents or by recrystallization or chromatographically.

The (−)-antipode of (E)-1-cyclohexyl-4,4-dimethyl-3-hydroxy-2-(1,2,4-triazol-1-yl)-pent-1-ene of the formula (I) which can be prepared by the process according to the invention and its use for regulating plant growth are known. See U.S. Pat. No. 4,592,772, issued Jun. 3, 1986.

The process according to the invention is illustrated by the following examples.

PREPARATION EXAMPLES

EXAMPLE 1

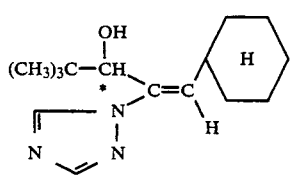
(I)

29 ml (0.029 mol) of boron hydride-tetrahydrofuran complex are added to a solution of 4.1 g (0.0145 mol) of S-2-(dibenzyl-hydroxymethyl)-pyrrolidine in 30 ml of absolute tetrahydrofuran at 20° C., with stirring. After the mixture has been stirred at 20° C. for 30 minutes, 2.61 g (0.01 mol) of the (E)-isomer of 1-cyclohexyl-4,4-dimethyl-2-(1,2,4-triazol-1-yl)-pent-1-en-3-one are added and the mixture is stirred at 40° C. for a further 16 hours. Thereafter, the reaction mixture is poured into 100 ml of 2N aqueous hydrochloric acid. The mixture formed is extracted twice with methylene chloride and the combined organic phases are concentrated under reduced pressure. The residue which remains is chromatographed with a mixture of chloroform/ethyl acetate=4:1 on silica gel. 2.3 g (87% of theory) of the (−)-antipode of (E)-1-cyclohexyl-4,4-dimethyl-3-hydroxy-2-(1,2,4-triazol-1-yl)-pent-1-ene are obtained in this manner in the form of a crystalline product.

Melting point: 150° C.
$[\alpha]_D^{20} = -61.4°$ (c=0.520/CHCl$_3$)
The product has an optical purity of 83% e.e.

EXAMPLE 2

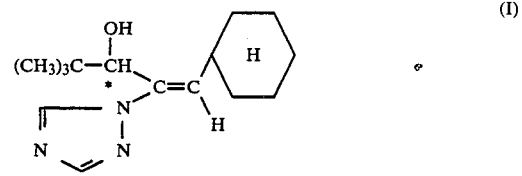
(I)

0.68 g (0.018 mol) of sodium boranate is added to a suspension of 5.2 g (0.018 mol) of S-2-(dibenzyl-hydroxymethyl)-pyrrolidine hydrochloride in 75 ml of absolute tetrahydrofuran at −30° C., with stirring. The temperature is allowed to rise gradually to 20° C. and stirring is continued at 20° C. for a further 2 hours. Thereafter, 3.15 g (0.012 mol) of the (E)-isomer of 1-cyclohexyl-4,4-dimethyl-2-(1,2,4-triazol-1-yl)-pent-1-en-3-one are added dropwise and the mixture is stirred at 40° C. for 20 hours. The reaction mixture is then poured into water. The resulting mixture is extracted with ethyl acetate and the combined organic phases are concentrated under reduced pressure. The residue which remains is chromatographed with a mixture of chloroform/ethyl acetate=4:1 on silica gel. 2.1 g (67% of theory) of the (−)-antipode of (E)-1-cyclohexyl-4,4-dimethyl-3-hydroxy-2-(1,2,4-triazol-1-yl)-pent-1-ene are obtained in this manner in the form of a crystalline product.

Melting point: 148°–150° C.
$[\alpha]_D^{20}: -62.3°$ (c=0.464/CHCl$_3$)
The product has an optical purity of 79.3% e.e. (according to chromatographic determination).

EXAMPLE 3

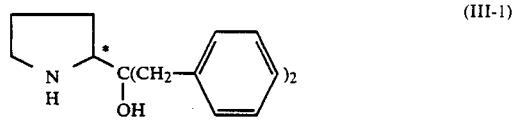
(III-1)

13 g (0.1 mol) of S-proline methyl ester are added dropwise, while stirring and cooling with ice, to a Grignard compound prepared from 25 g (1 mol) of magnesium and 127 g (1 mol) of benzyl chloride in 350 ml of ether. The reaction mixture is warmed and is boiled under reflux for 2 hours. Thereafter, hydrolysis is carried out by slow addition of water. The reaction mixture thus formed is poured into 1.5 liters of saturated aqueous ammonium chloride solution. The organic phase is separated off and the aqueous phase is extracted once again with ether. The combined organic phases are washed with dilute aqueous sodium hydroxide solution and then dried and concentrated under reduced pressure. The residue which remains is distilled under a high vacuum. 19.7 g (70% of theory) of S-2-(dibenzyl-hydroxymethyl)-pyrrolidine are obtained in this manner in the form of a liquid.

Boiling point: 165°–170° C./0.03 mbar
$[\alpha]_D^{20} = +9.6°$ (c=0.581/CH₃OH)

EXAMPLE 4

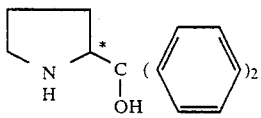
(III-2)

13 g (0.1 mol) of S-proline methyl ester are added dropwise, while stirring and cooling with ice, to a Grignard compound prepared from 25 g (1 mol) of magnesium and 157 g (1 mol) of bromobenzene in 350 ml of ether. The reaction mixture is warmed, and is boiled under reflux for 2 hours. Thereafter, hydrolysis is carried out by slow addition of water. The reaction mixture thus formed is poured into 1.5 liters of saturated aqueous ammonium chloride solution. The combined organic phases are washed with dilute aqueous sodium hydroxide solution and then dried and concentrated under reduced pressure. The residue which remains is chromatographed with ethyl acetate on silica gel. 10.8 g (22% of theory) of S-2-(diphenylhydroxymethyl)-pyrrolidine are obtained in this manner in the form of a viscous product.

EXAMPLE 5

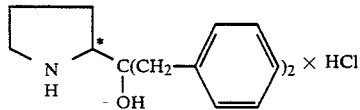
(III-3)

1st stage

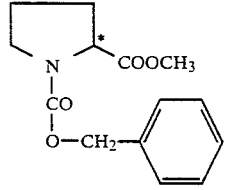
(VII-1)

180 g (1.01 mol) of benzyl chloroformate are added dropwise to a solution of 130 g (1 mol) of S-proline methyl ester and 155 ml (1.1 mol) of triethylamine in 600 ml of absolute tetrahydrofuran at a temperature between 0° C. and 10° C., while stirring, a colorless precipitate separating out. The reaction mixture is left to stand at room temperature for 16 hours and is then poured into 1.5 liters of water. The resulting mixture is extracted several times with ethyl acetate. The combined organic phases are washed first with dilute aqueous hydrochloric acid and then with water and are concentrated under reduced pressure. The residue which remains is distilled under a high vacuum. 188 g (72% of theory) of N-benzyloxycarbonyl-S-proline methyl ester of boiling point 160° C./0.1 mbar are obtained in this manner.

2nd stage

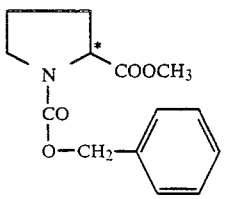
(VII-1)

A solution of 87 g (0.33 mol) of N-benzyloxycarbonyl-S-proline methyl ester in 200 ml of absolute ether is added dropwise, while stirring and at 0° C., to a Grignard compound prepared from 28 g (1 mol) of magnesium and 171 g (1 mol) of benzyl bromide in 400 ml of absolute ether. The reaction mixture is left to stand at room temperature for 16 hours and is then hydrolyzed by addition of water. It is then acidified with concentrated hydrochloric acid and extracted with ethyl acetate. The combined organic phases are washed with water, dried and concentrated under reduced pressure. 163 g of a yellow oil which, according to the gas chromatogram, consists of N-benzyloxycarbonyl-S-2-(dibenzyl-hydroxymethyl)-pyrrolidine to the extent of 50%, are obtained in this manner. The yield is accordingly calculated as 59.9% of theory.

3rd stage

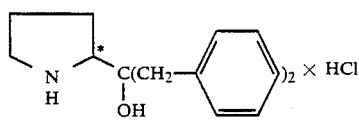
(III-3)

A solution of 75 g of the crude product containing 50% of N-benzyloxycarbonyl-S-2-(dibenzyl-hydroxymethyl)-pyrrolidine in 300 ml of ethanol is hydrogenated with 10 g of palladium-on-charcoal (5% strength) with hydrogen under a pressure of 5 bar at 20° C. for 5 hours. After the catalyst has been filtered off with suction, a vigorous stream of hydrogen chloride is passed into the solution, while cooling. The reaction mixture is then concentrated by stripping off the solvent under reduced pressure and 300 ml of ethyl acetate are added to the oily product which remains. The precipitate which thereby crystallizes out is filtered off with suction. 25 g (87.5% of theory, based on a 50% pure starting substance) of S-2-(dibenzyl-hydroxymethyl)-pyrrolidine hydrochloride are obtained in this manner.

Melting point: 130° C.

Treatment of the salt thus prepared with dilute aqueous sodium hydroxide solution gives free S-2-(dibenzyl-hydroxymethyl)-pyrrolidine, which is identical to the product described in Example 3.

It is understood that the specification and examples are illustrative but not limitative of the present invention and that other embodiments within the spirit and scope of the invention will suggest themselves to those skilled in the art.

I claim:

1. The opically active compound of the formula

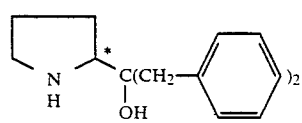
(III-1)

or the hydrochloric acid addition product thereof.

* * * * *